United States Patent [19]

Fuisz

[11] Patent Number: 5,516,537
[45] Date of Patent: May 14, 1996

[54] FROZEN COMESTIBLES

[75] Inventor: Richard C. Fuisz, Great Falls, Va.

[73] Assignee: Fuisz Technologies Ltd., Chantilly, Va.

[21] Appl. No.: 331,628

[22] PCT Filed: May 4, 1993

[86] PCT No.: PCT/US93/04362

§ 371 Date: Feb. 21, 1995

§ 102(e) Date: Feb. 21, 1995

[87] PCT Pub. No.: WO93/21789

PCT Pub. Date: Nov. 11, 1993

Related U.S. Application Data

[63] Continuation-in-part of Ser. No. 851,650, Mar. 16, 1992, Pat. No. 5,236,734, which is a continuation-in-part of Ser. No. 602,485, Oct. 24, 1990, Pat. No. 5,096,492, which is a continuation-in-part of Ser. No. 169,838, Mar. 18, 1988, Pat. No. 4,855,326, which is a continuation-in-part of Ser. No. 40,371, Apr. 20, 1987, abandoned.

[51] Int. Cl.$^6$ .................................................. A23G 9/02
[52] U.S. Cl. .......................... 426/100; 426/565; 426/567
[58] Field of Search .................................... 426/100, 565, 426/567, 658

[56] References Cited

U.S. PATENT DOCUMENTS

| | | |
|---|---|---|
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,118,396 | 1/1964 | Brown et al. . |
| 3,131,428 | 5/1964 | Mika . |
| 3,308,221 | 3/1067 | Opfell . |
| 3,324,061 | 6/1067 | Tanquary et al. . |
| 3,482,998 | 12/1969 | Carroll et al. . |
| 3,523,889 | 8/1970 | Eis . |
| 3,557,717 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,676,148 | 7/1972 | De Weese et al. . |
| 3,723,134 | 3/1973 | Chivers . |
| 3,762,846 | 10/1973 | Chivers . |
| 3,766,165 | 10/1973 | Rennhard . |
| 3,856,443 | 12/1974 | Salvi . |
| 3,875,300 | 4/1975 | Homm et al. . |
| 3,876,794 | 4/1975 | Rennhard . |
| 3,925,525 | 12/1975 | LaNieve . |
| 3,930,043 | 12/1975 | Warning et al. . |
| 3,951,821 | 4/1976 | Davidson . |
| 3,967,623 | 7/1976 | Butterworth et al. . |
| 3,972,725 | 8/1976 | Nicol . |
| 3,981,739 | 9/1976 | Dmitrovsky et al. . |
| 3,992,265 | 11/1976 | Hansen . |
| 4,056,364 | 11/1977 | Dmitrovsky et al. . |
| 4,086,418 | 4/1978 | Turbak et al. . |
| 4,090,920 | 5/1978 | Studer, Jr. . |
| 4,136,145 | 1/1979 | Fuchs et al. . |
| 4,153,512 | 5/1979 | Messner et al. . |
| 4,159,210 | 6/1979 | Chen et al. . |
| 4,293,570 | 10/1981 | Vadesz . |
| 4,303,684 | 12/1981 | Pitchon et al. . |
| 4,338,350 | 7/1982 | Chen et al. . |
| 4,348,420 | 9/1982 | Lynch et al. . |
| 4,362,757 | 12/1982 | Chen et al. . |
| 4,371,516 | 2/0183 | Gregory et al. . |
| 4,376,743 | 3/1983 | Dees . |
| 4,382,963 | 5/1983 | Klose et al. . |
| 4,492,685 | 1/1985 | Keith et al. . |
| 4,496,592 | 1/1985 | Kuwahara et al. . |
| 4,500,546 | 2/1985 | Turbak et al. . |
| 4,504,509 | 3/1985 | Bell et al. . |
| 4,511,584 | 4/1985 | Percel et al. . |
| 4,526,525 | 7/1985 | Oiso et al. . |
| 4,585,797 | 4/1986 | Cioca . |
| 4,619,833 | 10/1986 | Anderson . |
| 4,765,991 | 8/1988 | Cherukuri et al. . |
| 4,772,477 | 9/1988 | Cherukuri et al. . |
| 4,793,782 | 12/1988 | Sullivan . |
| 4,816,283 | 3/1989 | Wade et al. . |
| 4,853,243 | 8/1989 | Kahn et al. . |
| 4,855,326 | 8/1989 | Fuisz . |
| 4,872,821 | 10/1989 | Weiss . |
| 4,873,085 | 10/1989 | Fuisz . |
| 4,879,108 | 11/1989 | Yang et al. . |
| 4,885,281 | 12/1989 | Hanstein et al. . |
| 4,978,537 | 12/1990 | Song . |
| 4,988,529 | 1/1991 | Nakaya et al. . |
| 4,997,856 | 3/1991 | Fuisz . |
| 5,011,532 | 4/1991 | Fuisz . |
| 5,028,632 | 7/1991 | Fuisz . |
| 5,034,421 | 7/1991 | Fuisz . |
| 5,073,387 | 12/1991 | Whistler . |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0287488A1 | 3/1988 | European Pat. Off. . |
| 0387950A1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 91/18613 | 5/1991 | WIPO . |

OTHER PUBLICATIONS

Winder, W. C., *McGraw Hill Encyclopedia of Science and Technology,* 9, p. 1–3, 6th Ed. (1987).

Primary Examiner—Arthur L. Corbin
Attorney, Agent, or Firm—Hoffmann & Baron

[57] ABSTRACT

Frozen comestibles, such as frozen desserts, are formed by combining frozen comestible ingredients with a matrix resulting from melt-spinning on oleaginous substance with a carrier material.

27 Claims, No Drawings

U.S. PATENT DOCUMENTS

| | | |
|---|---|---|
| 5,077,076 | 12/1991 | Gonsalves et al. . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,173,322 | 12/1992 | Melachouris et al. . |
| 5,196,199 | 3/1993 | Fuisz . |
| 5,236,734 | 8/1993 | Fuisz . |
| 5,238,696 | 8/1993 | Fuisz . |
| 5,279,849 | 1/1994 | Fuisz et al. . |
| 5,286,513 | 2/1994 | Fuisz . |
| 5,288,508 | 2/1994 | Fuisz . |

FROZEN COMESTIBLES

BACKGROUND OF THE INVENTION

This application is a 371 of PCT/US93/04362, filed May 4, 1993 and a continuation-in-part of U.S. patent application Ser. No. 07/851,650, filed Mar. 16, 1992, now U.S. Pat. No. 5,236,734, which is a continuation-in-part of U.S. Ser. No. 07/602,485, filed Oct. 24, 1990, now U.S. Pat. No. 5,096,492 which, in turn, is a continuation-in-part of U.S. Ser. No. 07/169,838, filed Mar. 18, 1988, now U.S. Pat. No. 4,855,326 (the "'326" patent), which, in turn, is a continuation-in-part of U.S. patent application Ser. No. 040,371, filed Apr. 20, 1987, now abandoned. The disclosure of the '326 patent is incorporated herein by reference.

The present invention relates to new frozen comestibles, and, in a more particular aspect, it relates to low fat frozen desserts with the organoleptic characteristics of high fat frozen desserts. The invention also relates to methods of making the frozen comestibles.

Food technology in recent years has focused on providing high quality food products which are low in calorie content and low in cost. In this regard, the frozen dessert industry has attempted to provide reduced-fat products which have organoleptic properties similar to the same products having a normally higher fat content. This objective is particularly difficult to achieve in frozen food products because the product is subjected to low temperatures which can have an adverse effect on the blend of ingredients.

Ice cream, for example, is a frozen dessert recognized for its smooth, creamy texture achieved by delicately balancing formulated ingredients and processing steps to provide the desired coldness, melt-down, mouthfeel and other taste characteristics.

Primary components of ice cream products are the dairy-based ingredients. In earlier times, milk and cream provided the basic ingredients, i.e., milk protein, milk sugar, milkfat (butterfat), emulsifiers and stabilizers, necessary for making ice cream products. In current commercial operations, ice cream formulations can also include nonfat milk solids, milk fat, sugar and water to replace some or all of the traditional ingredient milk/cream, as well as other non-dairy ingredients such as egg yolks, emulsifiers and stabilizers.

By definition, ice cream must contain not less than 10% milk fat and 20% total milk solids. Unfortunately, milk fats add a significant amount of calories to the ice cream. Ice milks have been introduced to reduce the amount of calories in the product. Ice milks are formulated to be low in milk fat and to include primarily nonfat milk solids. Some ice milks, however, contain high percentages of nonfat milk solids which can impart a gritty or chalky mouthfeel. This drawback is chiefly due to the high levels of solids which do not melt in the oral cavity. In addition, the higher concentrations of crystallized lactose present in nonfat milk solids can also contribute to inferior organoleptic qualities.

Thus, ingredients and methods are constantly being sought to provide a reduced fat frozen comestible with a creamy texture and a lubriciousness characteristic of a higher fat content food product.

It is, therefore, a purpose of the present invention to provide a frozen food product which has organoleptic properties characteristic of a fat-containing product.

It is another purpose of the present invention to provide ice cream or ice milk products having substantially reduced fat content and a creamy texture which can be stored for relatively long periods of time without deterioration.

Other and further purposes of the present invention will become apparent in the following description and its scope will be pointed out with the appended claims.

SUMMARY OF THE INVENTION

The present invention includes frozen food products prepared with an oleaginous-containing matrix formed by melt-spinning an oleaginous substance with a carrier material. The oleaginous substances used in this invention can include edible oils such as vegetable oils including soybean, corn, canola and the like. Alternatively, fats such as meat fats, hydrogenated vegetable oils, and even butter fat can be used. The oleaginous substances make up from about 2 to about 40% by weight of the matrix, with amounts of from about 10 to about 30% being preferred and amounts of from about 15 to about 25% being most preferred.

Carrier materials which can be used for the matrix are saccharides such as sucrose or saccharide-based materials such as maltodextrins and/or water soluble cellulosic materials such as methyl and ethyl cellulose. In further aspects of the invention, the matrix includes one or more adjunct materials such as natural or artificial flavors, spices, sweeteners and/or hydrogels such as xanthan gum or alginates to enhance the matrix and/or products to which the matrix is included.

The oleaginous-containing matrix can be incorporated in a variety of frozen food products. For example, the matrix can be included with partially frozen or fully hardened homogenized pasturizing mixtures containing fat, milk solids other than fat, sweeteners, flavoring substances, emulsifiers and the like. Frozen desserts prepared in accordance with the present invention can be firm, solid products, or can be pumpable, semi-solid products such as soft-serve type products. Frozen desserts of the present invention also include, but are not limited to, products similar to conventional ice cream, frozen custards, i.e., the so called French ice creams, mellorines, ice milks and sherbets.

The present invention further includes the method of making frozen food products. The method includes subjecting a feedstock material and oleaginous substance to conditions of high temperature and shear sufficient to form a matrix which includes oleaginous materials. This oleaginous-bearing matrix can then be incorporated into the frozen food product. In order to prepare a frozen dessert, the matrix described above can be combined with a dessert material to provide various products such as ice-cream-like products.

The present invention also includes matrices composed of an oleaginous substance, a carrier material, and one or more ingredients that are commonly used in conventional frozen food products. It is preferred that these ingredients be substantially non-aqueous. Water is not an ingredient useful in forming these matrices. The matrix in this form may be consumed as the dry non-descript matrix or may be mixed with a liquid such as water, milk, a milk product, or the like, to form a creamy product which has a taste and texture approximating ice cream or other frozen food product. Products made in this way may be refrigerated or frozen if desired. Alternatively, the dry matrix may be compressed, by itself or in conjunction with additional dry ingredients, to tablet form that can be dissolved in the mouth or chewed, thereby also imparting the taste and texture qualities of a conventional frozen food product.

As a result of the present invention, frozen comestibles can be provided which have desirable organoleptic properties and a selected fat content. For example, ice-cream-like products can be made which are low in fat yet have a smooth, creamy and non-gritty mouthfeel similar to that of a fine custard. In addition, the creamy texture and smooth consistency can be maintained for long periods of storage.

In one particularly interesting aspect, a portion of the frozen food product's fat content is replaced with a matrix containing a much lower amount of fat without a detectable loss of flavor or mouthfeel. In certain products, up to 50% of the usual fat content can be replaced without compromising gustatory qualities.

DETAILED DESCRIPTION OF THE INVENTION

In the present invention, an oleaginous-bearing matrix can be formed by subjecting carrier feedstock and oleaginous substance to conditions of temperature and shear to form the matrix. This can be accomplished by melt-spinning oleaginous substances with carrier materials. The matrix is included in various low fat frozen products.

The spinning process is preferably carried out with "cotton candy" fabricating-type equipment. The spinning machine used herein can be any cotton candy-type machine such as the Econo Floss model 3017 manufactured by Gold Medal Products Company of Cincinnati, Ohio. It will be appreciated by those skilled in the art that any apparatus or physical process which provides similar forces and temperature gradient conditions can also be used. For simplicity in disclosing and describing this invention, the term "melt-spinning" will be understood to mean a flash-flow process which includes a combination of temperature, shear, flow, flow rate, mechanical forces and thermal gradients of the type used in a cotton candy-type machine. The apparatus is operated at a temperature and speed which permits flash flow but does not deteriorate the material undergoing the processing. Usually the resulting matrix product is in the form of a particle, flake, spicule, or other generally nondescript aggregate capable of subsequent incorporation into a frozen food product.

The melt-spinning process for producing the matrix includes introducing a mixture containing the oleaginous material and carrier simultaneously to conditions of high temperature and shear created by centrifugally forcing the ingredients through a small orifice. The extremely short amount of time during which the ingredients are exposed to the melt-spinning temperature and shear allows the matrix to be formed without adverse effects.

The flash flow process contemplates subjecting carrier solids to a melt-spin process (or conditions comparable thereto) which provide sufficient internal flow to permit the transition in structure without degradation of the material. Internal flow occurs when the infrastructure of the material breaks down sufficiently to permit movement of material at a subparticle level, and probably at a molecular level. At a molecular level, internal flow contemplates the movement of molecules relative to each other.

Therefore, apparatus other than cotton candy-type machines may be used in accordance with the present invention so long as the apparatus generates flash flow conditions sufficient to induce morphological and/or chemical transformation of the feedstock to produce the nondescript matrix. Such alternative apparatus is exemplified in U.S. Ser. No. 954,257, filed Sep. 30, 1992, now abandoned and U.S. Ser. No. 965,804, filed Oct. 23, 1992, now U.S. Pat. No. 5,380,473, each of which is incorporated herein by reference.

Internal flow of material is generally associated with melting point or glass transition point. However, it is contemplated that the combined application of heat and external force is sufficient to produce the flow at temperatures below the melting or glass transition point for most compositions.

This new matrix can be used alone or in combination with other ingredients as a means for dispersing the added ingredient throughout the material. For example, the particles, chips, flakes, spicules or combinations thereof can be used to disperse oleaginous materials which are otherwise relatively non-dispersable because of the physical characteristics of such materials.

The oleaginous substance is present in amounts of from about 2% to about 40% by weight of the matrix. Amounts of from about 10% to about 30% by weight of the matrix are preferred, while amounts of from about 15% to about 25% are most preferred.

In one aspect of the present invention, the oleaginous substance is a food-acceptable/edible oil. Such substances are selected from vegetable oil, vegetable fat, hydrogenated vegetable oil, soybean oil, safflower oil, olive oil, partially hydrogenated palm kernel oil, butter oil, corn oil, canola oil, sunflower oil, mixtures thereof, and the like. In this regard, the oleaginous materials preferably contain less than 30% saturated fats, with amounts of less than 20% being preferred and amounts of less than 15% being most preferred. The matrix of the invention, thus, advantageously allows the artisan to substitute or exchange "healthy" oils for a portion of the unhealthy saturated fats typically present in frozen food products without noticeably detracting from the organoleptic qualities of the products.

In a further aspect, the oleaginous substance can be a fat such as an edible animal fat, anhydrous milk fat, butter fat, lards, hydrogenated animal and/or vegetable oils, mixtures thereof and the like.

The carriers included in the matrix can be saccharide-based and/or water-soluble cellulosic materials or mixtures thereof. A non-limiting list of suitable saccharide carriers include sucrose, lactose, fructose, dextrose, sorbitol, manitol, maltose, synthetically-derived saccharide materials such as polydextrose, mixtures thereof, and the like. Alternative saccharide materials such as maltodextrins and/or corn syrup solids are also useful. Maltodextrins contain a mix of sugars and polysaccharides which range from long-chain oligomers resulting from starch hydrolysis to sugars having a low number of monomeric units. Please note that for purposes of this invention, applicant refers to maltodextrins and corn syrup solids as defined by the FDA collectively as maltodextrins. Suitable water-soluble cellulosic materials include methyl cellulose, ethyl cellulose, hydroxy methyl or ethyl cellulose, alkali salts of carboxy methyl cellulose and the like and mixtures thereof.

The maltodextrins of the present invention, however, have been selected as having unique properties for the purposes of the present invention. Specifically, the maltodextrin feedstock of the present invention includes a carrier component which is capable of being processed from a solid under flash flow conditions to a new solid having altered physical and/or chemical structure. Moreover, the maltodextrins of the present invention are the mixtures resulting from hydrolysis and which have a dextrose equivalent or D.E. of less than 40. In a preferred embodiment of the present invention the D.E. is between 20 and 40, and in yet another preferred embodiment the D.E. is between 10 and 20. This definition also includes corn syrup solids as defined by the FDA. Maltodextrins which are useful in the present invention include some products which are sold under the trademark MALTRIN®, a product of the Grain Processing Corporation of Muscatine, Iowa.

Maltodextrins themselves have been used as a nonfat additive. One of the greatest advantages of maltodextrins is that they do not act adversely on the intestinal tract. Consequently, they are particularly useful as a bulking agent and as a fat substitute. Moreover, maltodextrins are generally recognized as safe (GRAS) by the United States Food and Drug Administration.

The oleaginous material and carrier matrix material can be processed with additional component(s). Such additional component(s) are primarily related to the desired properties of the frozen comestible. The nature and amount of additional components used with the matrix materials will vary the properties of the final matrix such as by affecting taste, color, shape and/or size of the matrix.

Thus, in one aspect of the invention, frozen dessert ingredient materials can be combined with the matrix materials prior to melt-spinning. For example, a broad range of natural and artificial flavorant compositions and mixtures thereof are suitable. Flavorants are defined as including any one or more combinations of flavors, sweeteners and any other organoleptically perceivable materials. The flavors may be chosen from a wide range of natural and artificial flavors known to those of ordinary skill in the art. An illustrative list of such agents includes volatile oils, synthetic flavor oils, flavoring aromatics, oils, liquids, oleoresins or extracts derived from plants, leaves, flowers, fruits, nuts, fudges and combinations thereof, as well as other combinations of ingredients as can be found in the conventional fat-containing soft and hard frozen desserts.

With regard to sweeteners, the present invention contemplates the inclusion of both natural and artificial sweeteners including high intensity sweeteners such as saccharin, dipeptide sweeteners such as aspartame, chloro derivatives of sucrose such as Sucralose®, acesulfame and the like.

In short, it is contemplated that any suitable flavorant material may be included in the matrix of the present invention. Those skilled in the art will realize that the amount of the flavorant will depend upon the particular flavorant(s) selected and the preference of the artisan. It is contemplated, however, that the flavorant will be present in amounts of from about 0.01 percent to about 40 percent by weight of the matrix, with amounts from about 0.5 percent to about 15 percent being preferred.

Furthermore, ingredients such as nutritional supplements, frozen dessert conditioning agents, dehydrated vegetable and/or animal fluids, egg products, vitamins and/or minerals, preservatives, emulsifiers and the like and mixtures thereof may be added. In short, it is contemplated that any suitable food ingredient which is compatible with matrix formation and blending in the frozen product may be included in the matrix of the present invention.

In yet another embodiment of the invention, it is possible to incorporate emulsifiers such as those used in edible products in the saccharide-based matrix product. A nonlimiting list of such emulsifiers include mono- and diglycerides of fats, oils and fatty acids, propylene glycol esters of fats, lactylated fatty acids, polysorbates, polyglycerol esters, ethoxylated mono- and diglycerides, lecithin and the like and mixtures thereof. Other emulsifiers which are useful in frozen products of this nature are also contemplated for use in the present invention.

Those skilled in the art will realize that the above list is merely illustrative and not intended to exclude ingredients known to be within the scope of edible frozen dessert ingredients. The amount and combination of edible frozen dessert ingredients will depend upon the particular ingredients selected and the preference of the artisan.

In a further aspect of the present invention, the matrix may be formed by including a hydrogel with the other matrix ingredients during melt-spinning. Examples of suitable hydrogels include gums such as xanthan gum, guar gum, carrageenan gum, gum tragacanth, alginates such as sodium alginate, gum karaya, locust bean gum, gum acacia, mixtures thereof and the like. The hydrogel can be present in amounts of from about 0.2 to about 4 percent by weight of the matrix, with amounts of from about 0.8 to about 2.5 percent being preferred.

The addition of hydrogels to the melt-spun matrix serves to enhance the mouthfeel of the fat substitute, improve the texture, and improve stability of the melt-spun matrix. Other enhanced characteristics are obtained by including edible fatty emulsifying agents such as monoglycerides, lecithin, triglycerides, polysorbates or mixtures thereof. Such ingredients can be included as part of the spun matrix or as part of the food product.

In these alternative aspects, the matrix is prepared by uniformly mixing all flavorants and any hydrogel and thereafter adding the oleaginous materials. Carrier materials are combined with the above mixture and the resultant combination is melt-spun.

The oleaginous-containing matrix is especially well-suited for frozen dessert products because substantially lower amounts of fats and oils can be dispersed in the frozen dessert without compromising the creamy texture, smooth appearance and other organoleptic properties of the final product. The matrix will be present in the product in amounts of from about 0.5 to about 20% by weight of the final products, with amounts of from about 1 to about 12% being preferred, and amounts of from about 3 to about 6% being most preferred.

The oleaginous-containing matrix can be combined with a wide variety of frozen dessert products such as French ice-cream, frozen custard, ice milk, sherbet, yogurt, frozen dairy confection, dietary frozen dairy dessert and mellorine or imitation ice cream. In addition, the matrix may be combined with frozen dessert materials such as soy or vegetable-based materials. Examples of such products include Toffuti®. It is contemplated that the inventive matrix can be combined with most frozen desserts to provide enhanced flavor including those products containing flours and starches, such as frozen cakes, jelly-rolls, etc.

Oleaginous material carried by the matrix can also be incorporated as a colloidal dispersion. In this aspect of the invention, a sufficient quantity of the oleaginous matrix flakes, floss or spicules are dispersed in a liquid such as water and/or a milk or non-dairy broth to form a dispersion. The dispersion can then be incorporated into the comestible composition to provide the desired characteristic(s). This feature enhances the ability to implement this invention and brings a degree of predictability and reproducibility to the method and product.

A colloidal dispersion of corn oil, peanut oil, canola oil or safflower oil was prepared by spinning a mixture of 20% of the respective oil and 80% sucrose at 3600 r.p.m. and 200°

C. The product was then dispersed in water and was used to produce frozen desserts having a significantly improved texture and mouthfeel.

In another embodiment, peanut butter flakes made by melt-spinning a mixture of peanut butter with either a maltodextrin or sucrose can be used to flavor the frozen dessert.

In yet another embodiment, the oleaginous-containing matrix and optionally the peanut butter flakes are added to the frozen dessert during the freezing step after the point at which the frozen dessert mixture loses its liquid characteristics i.e., after the point at which the mixture is sufficiently viscous to remain on a vertically held spoon for at least a second.

In another embodiment, a dry comestible product may be produced that includes a matrix of a carrier material, an oleaginous substance and one or more ingredients that are commonly found in conventional frozen desserts. Such suitable ingredients and conventional frozen desserts are described in detail elsewhere herein. Matrices formed in accordance with this embodiment exhibit organoleptic qualities approximating those of such conventional frozen desserts but exhibit very long shelf life at ambient temperatures, requiring to refrigeration.

Matrices produced in accordance with this embodiment may be used in a variety of ways. For example, the matrix may be combined with a comestible liquid such as water, skim milk, low fat milk, whole milk, condensed milk, evaporated milk, reconstituted dry milk, cream, an aqueous emulsion of a food oil, other non-dairy broth or mixtures thereof. The comestible liquid imparts flow and texture consistency to the matrix when used in sufficient quantities, producing slurries or liquids such as, for example, a product that may be characterized as a room-temperature milk shake. Matrices in combination with such comestible liquids may also be refrigerated or frozen, at temperatures ranging from about −20° C. to about below ambient temperature. When frozen, such combinations yield products having organoleptic qualities approximating those of ice cream and other frozen desserts.

Alternatively, such matrices may be consumed in a dry form, either as a loose non-descript matrix, e.g., flakes, or compressed into tablet form, yielding a product which, when dissolved in the mouth or chewed, produces a very pleasant creamy taste and texture. A variety of tablet forming procedures may be used, such as wet granulation, dry granulation, and direct compression. Direct compression tablet forming techniques are preferred since the matrix is preferably readily dissolved upon contact with the mouth, and is preferably chewable. In a direct compression technique, the matrix and any additives present are directed to a series of die cavities, followed by compression of each of the quantities of material into compressed tablets. The resulting compressed tablet is generally an excellent tablet which dissolves and/or breaks apart readily, providing maximum surface area to the user.

Frozen dessert compositions made by adding the oleaginous matrix or a flavored matrix such as a matrix containing peanut butter or a cherry flavoring near the end of the freezing step have new and unusual taste qualities which appeal to certain taste panels. The flavored matrixes can be added to a frozen dessert such as a vanilla flavored frozen dessert to provide two distinct flavors, such as cherry-vanilla which appeals to many consumers.

It has been surprisingly found that exceptionally tasty frozen dessert products can be prepared by exchanging a portion of the fat typically present in the frozen dessert with a matrix which carries a reduced amount of fat. In this aspect, the low calorie frozen dessert products of the present invention obtained by substituting a portion of the fat with the matrix of the invention have a smooth, creamy, nongritty mouth feel that is more like that of a conventional high fat content ice cream product.

For example, in a conventional reduced-fat ice cream product a portion of the normal level of fat has been removed. The end composition is generally from about 7% to about 10% fat. However, when the oleaginous-containing matrix of the present invention is used, the fat content can be further reduced to about 2% to about 5% of the overall composition of the product. For example, a spun matrix containing a mixture of 20% oleaginous material and 80% carrier can be combined with either a low-fat ice cream mix or a nonfat ice-cream mix to provide most of the same organoleptic qualities but with substantially less fat in the overall product.

An additional advantage of the present invention is the unexpected ability of the matrix to extend the storage shelf-life of the frozen desserts it is contained in. While applicant is not bound by theory, it appears that the oleaginous-containing matrix of the present invention has an antioxidant and bactericidal effect in the frozen product in which it has been incorporated. Moreover, neither coagulation, congealing, separations, recrystallization nor any other texture-deteriorating effects occur to the extent that organoleptic perception suffers. A creamy smooth texture can be maintained for long periods of storage.

The carrier, oleaginous material and, other additives, such as flavorant(s) or hydrogels can be combined to be part of the matrix. Additional materials can be uniformly mixed; the oleaginous substance is thereafter combined, preferably as a liquid, with the ancillary materials mixture; the carrier is added to the combination and thoroughly mixed; finally, the ingredients are spun in a melt-spinning-type machine such as that described herein to produce a matrix in the form of a floss, chip, spicule or the like. The matrix is then combined with frozen food ingredients.

The frozen products in which the matrix is incorporated can also include ancillary materials such as colorants, preservatives, dyes and the like. Such materials may be included in addition to or in lieu of those ancillary materials included in the matrix. Suitable auxiliary agents may be selected from any of the numerous food-acceptable materials known to those with ordinary skill in the art and may be included in amounts also known to the artisan.

EXAMPLES

The following examples serve to provide further appreciation of the invention, but are not meant in any way to restrict the effective scope of the invention. Unless indicated otherwise, the Econo Floss machine referred to above was used to form the spun-matrix. Operating temperatures were approximately 200° C., and spinning speed was approximately 3,600 r.p.m.

without experiencing recrystallization or organoleptically perceptible deterioration.

TABLE I

| Ingredients | Desired CWT = 1.94 Fluid, i.e., Wet Wt. LBS/BATCH | GALS | Solids, per cwt | Rel. Sweet | Wet Wht., lbs. per cwt | Fat Solids lb/cwt | Serus Solids lb/cwt | Sweetner Solids lb/cwt | Stab. Solids lb/cwt | Whey Solids lb/cwt | Other Solids lb/cwt |
|---|---|---|---|---|---|---|---|---|---|---|---|
| Nonfat dry milk | 5.5 | 1 | 2.73 | | 2.81 | 0.03 | 2.70 | | | | |
| Cream, Heavy (ca 40%) | 14.3 | 2 | 3.31 | | 7.34 | 2.93 | 0.38 | | | | |
| Milk, Skim | 156.4 | 18 | 6.96 | | 80.49 | 0.04 | 6.92 | | | | |
| Cane Sugar (Sucrose) | 17.2 | | 8.80 | 8.80 | 8.84 | | | 8.80 | | | |
| Stabilizer/Emulsifier No. 1 | 0.5 | | 0.25 | | 0.26 | | | | 0.25 | | |
| Stabilizer/Emulsifier No. 2 | 0.5 | | 0.25 | | 0.26 | | | | 0.25 | | |
| Matrix of Example 1 | 16.0 | | 99.7 | 6.2 | n/a | 2.0 | 0.0 | 6.2 | 0.0 | 0.0 | |
| Pounds of mix | 210.3 | | | 15.0 | 100.0 | 5.0 | 10.0 | 15.0 | 0.5 | 0.0 | 0.0 |
| Gallons of mix | 21.7 | | | | | | | | | | |
| | LBS/CWT SPECIFIED: | | 22.30 | | | 3.00 | 10.00 | 8.80 | 0.50 | 0.00 | |
| | LBS/CWT CALCULATED: | | 22.30 | | | 3.00 | 10.00 | 8.80 | 0.50 | 0.00 = LBS/CWT | |
| | LBS/BATCH: | | 43.33 | | | 5.83 | 19.43 | 17.10 | 0.97 | 0.00 = LBS/BATCH | |

Example 1

25% Fat Matrix

In this example, butter oil and corn oil were combined with sucrose and processed to form a matrix as set forth below for incorporating in a frozen food product. Normally, butter oil and corn oil are substantially nondispersible. Consequently, a mixture such as that set forth in this example would not be a likely candidate for dispersing in a food product, especially a frozen food product where the inability to effect thorough mixing is exacerbated by freezing the product.

| Ingredients | Weight Percent | Weight (lbs) |
|---|---|---|
| Butter Oil | 12.5 | 2.0 |
| Corn Oil | 12.5 | 2.0 |
| Sucrose | 75.0 | 12.0 |

All of the ingredients were first thoroughly mixed. The resulting mixture was subjected to elevated temperatures and shear of the Econo Floss machine to provide the oleaginous-containing matrix.

Example 1A

The matrix obtained in Example 1 was incorporated into a 10 gallon mixture of low calorie ice cream as set forth in Table I. The total amount of oleaginous substance in the resulting product was about 5% of the overall composition. Ice-cream normally contains about 12 to 16% fat. Thus, the frozen product of the present invention contained about 60% reduction in oleaginous substance.

The product itself was a velvety, fine custard of creamy textured ice-cream. Moreover, the product maintained its texture for long periods of storage , e.g., about 1 year,

Example 2

32% Fat Matrix

In this example, to form the matrix set forth below, only 8% corn oil was mixed with a combined carrier feedstock of polydextrose and sucrose. The mixture was spun at 200° C. and 3600 r.p.m. Once again, corn oil is not generally considered an ingredient which is readily mixed in any composition, let alone one which will be frozen and stored. However, the unique features of the present invention enable the artisan to cut against conventional thinking to provide an easily dispersible matrix in a product which will not deteriorate.

| Ingredients | Weight Percent | Weight (lbs) |
|---|---|---|
| Corn Oil | 8% | 1.0 |
| Polydextrose | 20% | 2.5 |
| Sucrose | 72% | 9.0 |

The ingredients were thoroughly mixed and subject to the rigors of the spinning apparatus simultaneously as a mixture. The resulting matrix was a substantially homogenous white floss which was easy to mix in a composition.

Example 2A

The matrix obtained in Example 2 was incorporated into a 10 gallon mixture of low calorie ice cream as set forth in Table II. The resulting composition contained only about 2% of oleaginous substance as compared to 12 to 16% of fat found in normal ice-cream.

As in Example 1A, the product was a velvety, fine custard which retained its texture even after a long period of storage, e.g., 1 year.

TABLE II

| Ingredients | Desired CWT = 1.96 Fluid, i.e., Wet Wt. LBS/BATCH | GALS | Solids, per cwt | Rel. Sweet/ cwt | Wet Wht., lbs. per cwt | Fat Solids lb/cwt | Serus Solids lb/cwt | Sweetner Solids lb/cwt | Stab. Solids lb/cwt | Whey Solids lb/cwt |
|---|---|---|---|---|---|---|---|---|---|---|
| Nonfat dry milk | 5.5 | 1 | 2.74 | | 2.82 | 0.03 | 2.71 | | | |
| Cream, (HALF & HALF) | 26.8 | 3 | 2.49 | | 13.70 | 1.44 | 1.05 | | | |
| Milk, (SKIM-MILK) | 142.0 | 17 | 6.27 | | 72.51 | 0.04 | 6.23 | | | |
| Cane Sugar (Sucrose) | 20.5 | | 10.40 | 10.40 | 10.45 | | | 10.40 | | |
| Stabilizer/ Emulsifier No. 1 | 0.5 | | 0.25 | | 0.26 | | | | 0.25 | |
| Stabilizer/ Emulsifier No. 2 | 0.5 | | 0.25 | | 0.26 | | | | 0.25 | |
| Matrix of Example 2 | 12.5 | 0.0 | 79.9 | 4.6 | n/a | 0.5 | 0.0 | 4.6 | 0.0 | 0.0 |
| Pounds of mix | 208.3 | | | 15.0 | 100.0 | 2.0 | 10.0 | 15.0 | 0.5 | 0.0 |
| Gallons of mix | | 21.7 | | | | | | | | |
| LBS/CWT SPECIFIED: | | | 22.40 | | | 1.50 | 10.00 | 10.40 | 0.50 | 0.00 |
| LBS/CWT CALCULATED: | | | 22.40 | | | 1.50 | 10.00 | 10.40 | 0.50 | 0.00 = LBS/CWT |
| LBS/BATCH: | | | 43.85 | | | 2.94 | 19.58 | 20.36 | 0.98 | 0.00 = LBS/BATCH |

Example 3

One cup of Gold Medal Jolly Berry® sugar and ⅛ cup of Crisco® vegetable oil were spun into a floss in accordance with the present invention. One ounce of Real Lucerne® instant non-fat dry milk was prepared by following the instructions on the package. One cup of the Crisco® oil-bearing floss, slightly compressed was then dissolved into the non-fat milk to form a rich colloidal mixture. The mixture was then frozen overnight. The product obtained had a smooth ice-cream/sherbet like consistency.

Example 4

⅛ cup of Crisco® vegetable oil and one cup of Domino® pure cane sugar were spun into an oil-bearing floss. A mixture was prepared to contain three cups of Dannon® non-fat yogurt, ½ tsp of McCormick® vanilla extract and the oil-bearing floss prepared according with this invention. The ingredients were placed in a Cuisinart® food processor having a soft plastic mixing blade and were mixed for one minute. The product was a thick and uniform creamy mixture. The mixture was then frozen overnight at 22° F. A creamy ice-cream-like frozen dessert was obtained.

Example 5

A mixture was prepared with one cup of sugar, ¼ cup of Dannon® non-fat yogurt, ¹⁄₁₆ cup of Crisco® vegetable oil and ½ tsp of vanilla extract. The ingredients were spun in accordance with the invention to obtain a floss. ½ cup of the floss and ½ ounce of water were placed into small containers which were then frozen overnight. A non-crystalline, creamy sherbet-like product was obtained.

Example 6

Two cups of Domino® cane sugar and ¼ cup of Crisco® vegetable oil were mixed with a spoon for a few minutes. A creamy milk mixture was prepared by mixing ¼ cup of Lucerne® non-fat dry milk powder with 1½ ounces of water. All ingredients and ½ tsp of vanilla extract were placed into a Cuisinart® food processor having a rubber mixing blade. The mixture was mixed in the Cuisinart® for one minute. The resulting product was thick and creamy. After being frozen overnight, a frozen dessert which tasted like ice cream was obtained.

In Examples 3–6 the saturated fat component of the frozen comestible has been significantly reduced by the use of the oleaginous based spun matrix. The result is cholesterol-free frozen desserts ranging from ice-cream to sherbet-like desserts which emulate the texture and mouthfeel of high fat frozen desserts.

Example 7

In this example, a control homemade vanilla ice-cream is prepared by using a commercially available recipe from Gaggia Gelatiera®. 50 grams of egg and 125 grams of sugar were hand-blended. 500 grams of whole milk, 190 grams of table cream, 5 ml of Trader Horn® vanilla flavor and a small package of Borden® salt were added to the sugar/egg mixture. The resulting mixture was blended for three minutes. This mixture was then placed into a Gaggia Gelatiera® reservoir, stirred and frozen for one cycle of the timer. The resulting ice-cream was crystalline and granular.

Example 8

200 grams of 25% corn oil, 4 ml of 0.5% natural butter flavor were spun with 596 grams of flossed sucrose to obtain the oleaginous-bearing matrix of the invention. One extra large egg (50 grams) was hand-blended with the above matrix. 700 grams of Giant Food® whole milk, 5 ml of Trader Horn® vanilla, and one small package of Borden® salt were added to the above mixture. The final mixture was blended for three minutes and was then placed into the Gaggia Gelatiera® ice-cream maker for one cycle of the timer. The resulting ice milk tasted less crystalline then the control sample prepared in the Example 7 and had a creamier consistency.

Example 9

200 grams of 25% corn oil, 4 ml of 0.5% natural butter flavor, 8 grams of 1% Durafax® 65, 8 grams of 1% Durafax® 80 and 580 of floss sucrose were spun into a floss according to the present invention. The spun matrix was then hand-blended with one 50 gram egg into a thick mixture. 700 grams of Giant Food® whole milk, 5 ml Trader Horn® vanilla extract and one small package of Borden® salt were blended for three minutes with the thick mixture obtained above. The final mixture was placed in the Gaggia Gelatiera® reservoir, stirred and frozen for one cycle of the timer. The resulting frozen dessert was very creamy and had a smooth texture.

Firm orange peel-like shavings could be made with a spoon from the frozen dessert obtained in Example 8. The frozen dessert had a rich mouthfeel, a strong buttery taste and smooth texture. The dessert had also a better surface gloss than the control sample of Example 7.

The frozen dessert obtained in Example 9 had an even smoother texture than the dessert obtained in Example 8. Shavings made with a spoon from the product obtained in Example 9 had a firm orange peel-like integrity similar to those obtained in Example 8. The surface gloss of the product obtained in Example 9 was better than that obtained in Example 8. The frozen dessert of Example 9 was smoother, had a stronger buttery taste and a richer mouthfeel than the frozen dessert obtained in Example 8.

Thus, frozen products prepared in accordance with the invention by using different oleaginous-bearing matrices yielded frozen desserts which were quite satisfactory to consumers.

Example 10

This example shows the preparation of a dry delivery product, having medium fat content, useful for the preparation of food products in accordance with the present invention.

| Ingredients | Weight, Grams |
| --- | --- |
| 1. Finely Ground Fructose | 60.0 |
| 2. Corn Syrup Solids (Hubinger DE42) | 132.0 |
| 3. Non-Fat Milk Solids (Carnation) | 90.0 |
| 4. Cream Solids (Dietrich Milk Prod.) | 6.0 |
| 5. Best Mix Stabilizer (Germantown Mfg.) | 1.35 |
| 6. Medium Chain Triglyceride Oil | 6.0 |
| 7. Vanilla | 3.0 |
| 8. Cream | 0.30 |
| 9. Carboxymethylcellulose (Aqualon) | 0.30 |
| 10. Sugar Gum (Supercol U NF, Aqualon) | 0.30 |

All ingredients except the medium chain triglyceride oil and the cream were blended in a Cuisinart® mixer. Then the triglyceride oil and the cream were added to the blend and mixed in thoroughly. The blend was then processed in a three inch diameter cable heater flash flow apparatus, as described in U.S. Ser. No. 954,257, at 3600 rpm with a cable temperature setting of approximately 105° C. Large white flakes of processed product were generated.

Fifty grams of the flake product was gently stirred into 150 grams of skim milk. The liquid mixture was poured into freezer trays and put in a freezer until solid. This procedure resulted in a frozen product having the taste and texture of a good frozen soft ice cream.

Fifty grams of the flake product was gently stirred into 75 grams of water and the resultant mixture was frozen to produce a frozen product having a taste and texture of a very acceptable frozen soft ice cream.

The flake product provides a dry delivery system which can be easily mixed with a comestible liquid such as water, milk or aqueous emulsion of a food oil to produce an acceptable product.

The processed flake matrix appears to provide a much more stable suspension of the ingredients in a liquid than the ingredients provide when blended but not processed. The unprocessed blend was compared to an equal amount of processed flakes, when each was added to skim milk in the above ratio. Upon four hours holding in a soft serve machine the unprocessed blend showed evidence of separation and breakdown whereas the sample made from processed flakes maintained its integrity and had a fuller creamier mouth feel.

These processed flakes have also been pressed into tablet form. When the tablets are put in the mouth they dissolve to produce a very pleasant creamy taste.

Example 11

This example shows the preparation of a dry delivery product, having low fat content, useful for the preparation of food products in accordance with the present invention.

| Ingredients | Weight, Grams |
| --- | --- |
| 1. Finely Ground Fructose | 60.0 |
| 2. Corn Syrup Solids (Hubinger DE42) | 138.0 |
| 3. Non-Fat Milk Solids (Carnation) | 90.0 |
| 4. Best Mix Stabilizer (Germantown Mfg.) | 1.35 |
| 5. Medium Chain Triglyceride Oil | 6.0 |
| 6. Vanilla | 3.0 |
| 7. Cream | 0.30 |
| 8. Carboxymethylcellulose (Aqualon) | 0.30 |
| 9. Sugar Gum (Supercol U NF, Aqualon) | 0.30 |

All ingredients except the medium chain triglyceride oil were blended in a Cuisinart® mixer. Then the triglyceride oil was added to the blend and mixed in thoroughly. The blend was then processed in a three inch diameter cable heater flash flow apparatus, as described in U.S. Ser. No. 954,257, now abandoned at 3600 rpm with a cable temperature setting of approximately 105° C. Large white flakes of processed product were generated.

Fifty grams of the flake product was gently stirred into 150 grams of skim milk. The liquid mixture was poured into freezer trays and put in a freezer until solid. This procedure resulted in a frozen product having the taste and texture of a good frozen soft ice cream.

Fifty grams of the flake product was gently stirred into 75 grams of water and the resultant mixture was frozen to produce a frozen product having a taste and texture of a very acceptable frozen soft ice cream.

The flake product provides a dry delivery system which can be easily mixed with a comestible liquid such as water, milk or aqueous emulsion of a food oil to produce an acceptable product.

The processed flake matrix appears to provide a much more stable suspension of the ingredients in a liquid than the ingredients provide when blended but not processed. The unprocessed blend was compared to an equal amount of processed flakes, when each was added to skim milk in the above ratio. Upon four hours holding in a soft serve machine the unprocessed blend showed evidence of separation and breakdown whereas the sample made from processed flakes maintained its integrity and had a fuller creamier mouth feel.

These processed flakes have also been pressed into tablet form. When the tablets are put in the mouth they dissolve to produce a very pleasant creamy taste.

Example 12

This example shows the preparation of a dry delivery product, having high fat content, useful for the preparation of food products in accordance with the present invention.

| Ingredients | Weight, Grams |
| --- | --- |
| 1. Finely Ground Fructose | 120.0 |
| 2. Corn Syrup Solids (Hubinger DE42) | 211.0 |
| 3. Non-Fat Milk Solids (Carnation) | 75.0 |
| 4. Cream Solids (Dietrich Milk Prod.) | 75.0 |
| 5. Best Mix Stabilizer (Germantown Mfg.) | 2.25 |
| 6. Medium Chain Triglyceride Oil | 10.0 |
| 7. Vanilla | 5.0 |
| 8. Carboxymethylcellulose (Aqualon) | 0.50 |
| 9. Sugar Gum (Supercol U NF, Aqualon) | 0.50 |

All ingredients except the medium chain triglyceride oil were blended in a Cuisinart® mixer. Then the triglyceride oil was added to the blend and mixed in thoroughly. The blend was then processed in a three inch diameter cable heater flash flow apparatus, as described in U.S. Ser. No. 954,257, now abandoned, at 3600 rpm with a cable temperature setting of approximately 105° C. Large white flakes of processed product were generated.

Fifty grams of the flake product was gently stirred into 150 grams of skim milk. The liquid mixture was poured into freezer trays and put in a freezer until solid. This procedure resulted in a frozen product having the taste and texture of a good frozen soft ice cream.

Fifty grams of the flake product was gently stirred into 75 grams of water and the resultant mixture was frozen to produce a frozen product having a taste and texture of a very acceptable frozen soft ice cream.

The flake product provides a dry delivery system which can be easily mixed with a comestible liquid such as water, milk or aqueous emulsion of a food oil to produce an acceptable product.

The processed flake matrix appears to provide a much more stable suspension of the ingredients in a liquid than the ingredients provide when blended but not processed. The unprocessed blend was compared to an equal amount of processed flakes, when each was added to skim milk in the above ratio. Upon four hours holding in a soft serve machine the unprocessed blend showed evidence of separation and breakdown whereas the sample made from processed flakes maintained its integrity and had a fuller creamier mouth feel.

These processed flakes have also been pressed into tablet form. When the tablets are put in the mouth they dissolve to produce a very pleasant creamy taste.

While there have been described what are presently believed to be the preferred embodiments of the invention, those skilled in the art will realize that changes and modifications may be made thereto without departing from the spirit of the invention, and it is intended to claim all such changes and modifications as far within in the true scope of the invention.

What is claimed is:

1. A frozen comestible, comprising frozen comestible ingredients and a matrix formed by melt-spinning an oleaginous substance with a carrier material to provide internal flow thereby permitting transition in structure without degradation of said oleaginous substance and carrier material.

2. The frozen comestible of claim 1, wherein said oleaginous substance is less than 30% saturated.

3. The frozen comestible of claim 1, wherein said oleaginous substance is less than 20% saturated.

4. The frozen comestible of claim 1, wherein said oleaginous substance is less than 15% saturated.

5. The frozen comestible of claim 1, wherein said oleaginous substance is selected from the group consisting of vegetable oil, vegetable fat, hydrogenated vegetable oil, partially hydrogenated palm kernel oil, soybean oil, canola oil, corn oil and mixtures thereof.

6. The frozen comestible of claim 1, wherein said oleaginous substance is selected from the group consisting of animal fats, anhydrous milk fat, lard, butter oil and mixtures thereof.

7. The frozen comestible of claim 1, wherein said oleaginous substance is selected from the group consisting of vegetable oil, vegetable fat, hydrogenated vegetable oil, partially hydrogenated palm kernel oil, soybean oil, canola oil, corn oil, sunflower oil, safflower oil, olive oil, animal fats, anhydrous milk fat, lard, butter oil and mixtures thereof.

8. The frozen comestible of claim 7, wherein said oleaginous substance is present in an amount of from about 2 to about 40% by weight of said matrix.

9. The frozen comestible of claim 8, wherein said oleaginous substance is present in an amount of from about 10 to about 30% by weight of said matrix.

10. The frozen comestible of claim 9, wherein said oleaginous substance is present in an amount of from about 15% to about 25% by weight of said matrix.

11. The frozen comestible of claim 1, wherein said carrier material is selected from a group consisting of saccharides, water soluble cellulosic materials and mixtures thereof.

12. The frozen comestible of claim 11, wherein said saccharide is selected from the group consisting of sucrose, lactose, fructose, dextrose, sorbitol, mannitol, maltose, and mixtures thereof.

13. The frozen comestible of claim 11, wherein said saccharide is selected from the group consisting of polydextrose, maltodextrins and mixtures thereof.

14. The frozen comestible of claim 11, wherein said carrier material is selected from the group consisting of methyl cellulose, ethyl cellulose, hydroxy methyl cellulose, hydroxy ethyl cellulose, alkali-metal salts of carboxy methyl cellulose and mixtures thereof.

15. The frozen comestible of claim 1, wherein said matrix is present in an amount of from about 0.5% to about 20% by weight of said comestible.

16. The frozen comestible of claim 15, wherein said matrix is present in an amount of from about 1.0% to about 12%.

17. The frozen comestible of claim 16, wherein said matrix is present in an amount of from about 3% to about 6%.

18. The frozen comestible of claim 1, further comprising a member of the group consisting of ice cream, frozen custard, hard frozen ice milk, soft-serve ice milk, sherbet, water ice, frozen dairy confection, dietary frozen dairy dessert, mellorine, hard frozen yogurt, soft frozen yogurt, whipped toppings, frostings for cakes or cookies, dips and puddings.

19. The frozen comestible of claim 1, further comprising a flavorant selected from the group consisting of natural flavors, artificial flavors and mixtures thereof.

20. The frozen comestible of claim 1, wherein said matrix is formed by melt-spinning a member of the group consisting of flavorants and hydrogels with said oleaginous substance and said carrier material.

21. The frozen comestible of claim 20, wherein said hydrogel is selected from the group consisting of xanthan gum, guar gum, alginates, carrageenans, succinoglycans, scleroglycans, gelatin, pectins, locust bean gum, gum tragacanth, gum kayara, gum acacia and mixtures thereof.

22. The frozen comestible of claim 21, wherein said hydrogel is present in an amount of from about 0.5% to about 4% by weight of said matrix.

23. A reduced-fat frozen dessert product, comprising a frozen dessert product which has an expected fat content and a matrix formed by melt-spinning an oleaginous substance with a carrier material to provide internal flow thereby permitting transition in structure without degradation of said oleaginous substance and carrier material, said matrix mixed in said product which has an expected fat content in an amount such that the total amount of fat contained in said reduced-fat frozen dessert product is less than said expected fat content.

24. A comestible product approximating organoleptic qualities of conventional frozen food products, comprising: a matrix, formed by subjecting a mixture of a carrier material, an oleaginous substance and at least one ingredient used in said conventional frozen food products selected from the group consisting of ice cream, frozen custard, hard frozen ice milk, soft-serve ice milk, sherbet, water ice, frozen dairy confection, dietary frozen dairy dessert, mellorine, hard frozen yogurt, soft frozen yogurt, whipped toppings, frostings for cakes or cookies, dips and puddings to conditions of temperature and pressure sufficient to provide flash flow of said carrier material, thereby providing transformation of structure without degradation of said carrier material; and a liquid, which adds flow and texture consistency to said matrix, in an amount sufficient to provide said comestible product.

25. The comestible product of claim 24, wherein said comestible product has been refrigerated to a temperature of from about −20° C. to about below ambient temperature.

26. The comestible product of claim 24, further comprising an ingredient selected from the group consisting of natural and artificial flavorants, natural and artificial sweeteners, hydrogels, emulsifiers, nutritional supplements, dehydrated vegetable fluids, dehydrated animal fluids, egg products, vitamins, minerals, preservatives, frozen dessert conditioning agents, and mixtures thereof.

27. The comestible product of claim 24, wherein said liquid is selected from the group consisting of water, skim milk, low fat milk, whole milk, reconstituted dry milk, condensed milk, evaporated milk, cream, aqueous emulsions of food oils, non-dairy broths, and mixtures thereof.

* * * * *